US011906301B2

(12) United States Patent
Hasebe

(10) Patent No.: US 11,906,301 B2
(45) Date of Patent: Feb. 20, 2024

(54) THICKNESS EVALUATION METHOD OF CELL SHEET

(71) Applicant: SCREEN HOLDINGS CO., LTD., Kyoto (JP)

(72) Inventor: Ryo Hasebe, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 216 days.

(21) Appl. No.: 17/469,119

(22) Filed: Sep. 8, 2021

(65) Prior Publication Data
US 2022/0090909 A1    Mar. 24, 2022

(30) Foreign Application Priority Data
Sep. 23, 2020 (JP) ................................. 2020-158649

(51) Int. Cl.
| | |
|---|---|
| *G01B 9/02* | (2022.01) |
| *G01B 9/02055* | (2022.01) |
| *G01B 9/02002* | (2022.01) |
| *G01B 9/02001* | (2022.01) |

(52) U.S. Cl.
CPC ..... *G01B 9/02063* (2013.01); *G01B 9/02002* (2013.01); *G01B 9/02012* (2013.01); *G01B 9/02071* (2013.01); *G01B 9/02072* (2013.04); *G01B 9/02092* (2013.01)

(58) Field of Classification Search
CPC ............ G01B 9/02063; G01B 9/02002; G01B 9/02012; G01B 9/02071; G01B 9/02072; G01B 9/02092; G01B 9/02085; G01B 2290/65; G01B 9/02091; G01N 33/4833
See application file for complete search history.

(56) References Cited

U.S. PATENT DOCUMENTS

| | | | |
|---|---|---|---|
| 2007/0165234 A1* | 7/2007 | Podoleanu | G01B 9/02044 356/451 |
| 2014/0141499 A1* | 5/2014 | Nakajima | C12M 41/34 435/286.1 |
| 2017/0167847 A1 | 6/2017 | Jeyama et al. | |

FOREIGN PATENT DOCUMENTS

JP     2017-106849 A     6/2017

* cited by examiner

*Primary Examiner* — Hwa Andrew Lee
(74) *Attorney, Agent, or Firm* — Rimon, P.C.

(57) ABSTRACT

A thickness evaluation method of the cell sheet according to the invention includes tomographically imaging a cell sheet by optical coherence tomography and obtaining a thickness distribution of the cell sheet based on a result of the tomography imaging. A tomographic image corresponding to one cross section of the cell sheet is obtained by tomography imaging while scanning the light in a main scanning direction. The tomography imaging is performed in every time while moving an incident position of the light at a predetermined feed pitch in a sub-scanning direction, thereby a plurality of the tomographic images corresponding to a plurality of cross-sections are obtained. One-dimensional thickness distributions of the cell sheet in the corresponding cross-sections are obtained based on each of the plurality of tomographic images, and a two-dimensional thickness distribution of the cell sheet is obtained by interpolating the one-dimensional thickness distributions.

6 Claims, 9 Drawing Sheets

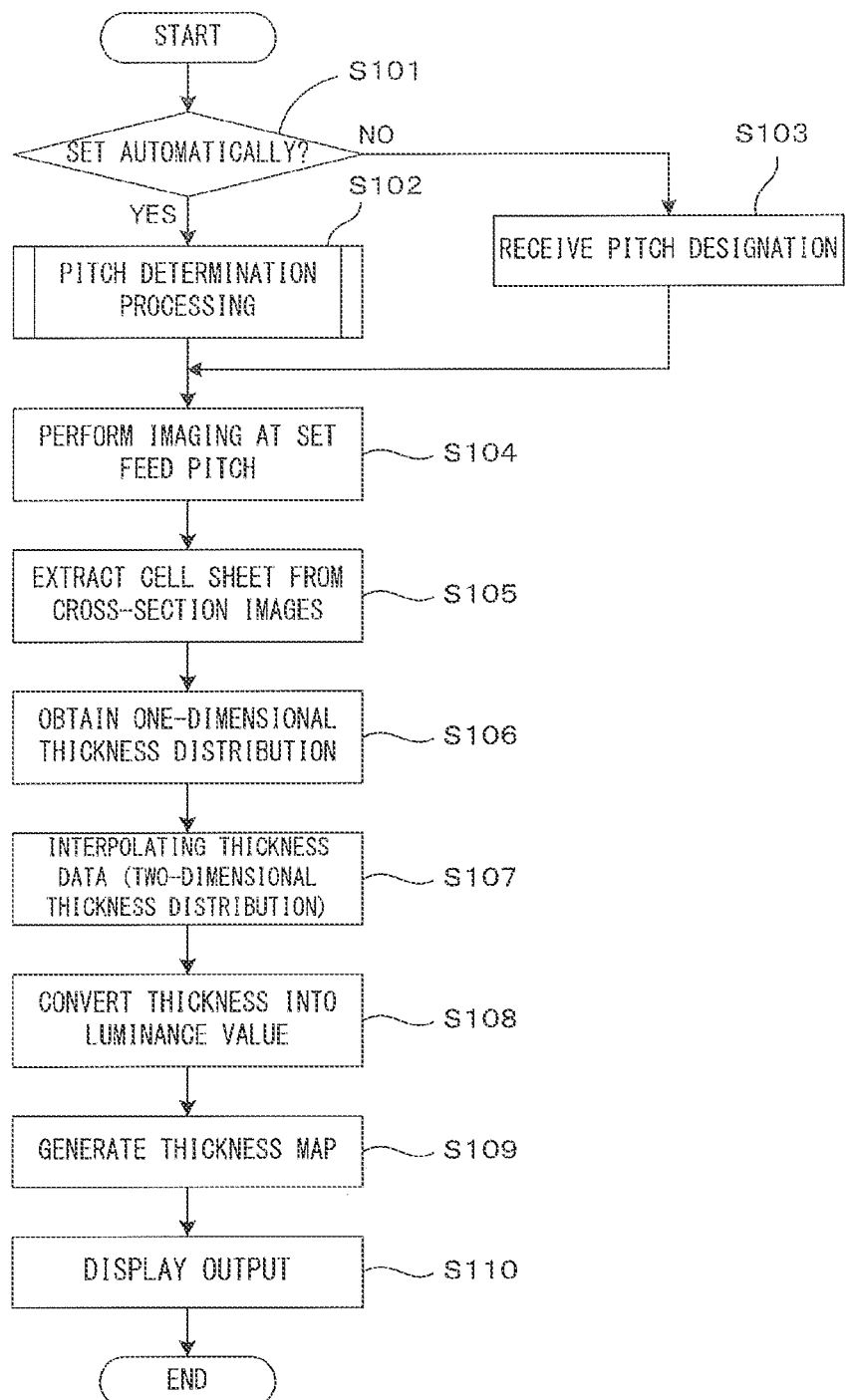

THICKNESS EVALUATION METHOD OF CELL SHEET

CROSS REFERENCE TO RELATED APPLICATION

The disclosure of Japanese Patent Application No.2020-158649 filed on Sep. 23, 2020 including specification, drawings and claims is incorporated herein by reference in its entirety.

BACKGROUND OF THE INVENTION

1. Field of the Invention

This invention relates to a method for imaging a cell sheet using the principle of optical coherence tomography imaging and obtaining a thickness distribution of the cell sheet.

2. Description of the Related Art

In technology fields of regenerative medicine and biochemistry, a cell sheet is, for example, used as an artificially cultured skin model. The cell sheet is, for example, a laminated sheet-like epidermal tissue formed in an insert well. A thickness of the cell sheet is measured as one of methods for knowing information representing which type of physiological properties (phenotype) the cell sheet has. Conventionally, a tissue section has been embedded in paraffin and a cross-section thereof has been observed and measured. However, because this method is an invasive method, the tissue cannot be continuously used thereafter. Further, due to the deformation of the tissue during embedding, the evaluation based on only parts appearing in the cross-section and the like, significant thickness information on the entire cell sheet cannot be necessarily obtained.

A method for tomographically imaging a cell sheet and evaluating a thickness of the cell sheet from image data is considered as a method for solving this problem. For example, an imaging apparatus described in JP 2017-106849A (patent literature 1) is an imaging apparatus of an optical coherence tomography (OCT) imaging type. In OCT imaging, low coherence light is caused to be incident on a specimen such as cells and interference light of diffuse reflection light from the specimen and reference light is detected, whereby a tomographic image of the specimen can be non-invasively captured. In such an imaging method, a three-dimensional structure of the specimen can be grasped. If a cell sheet is an object to be imaged, it is expected that a thickness can be accurately evaluated from an image of the cell sheet.

In this imaging technique, a three-dimensional image is obtained as follows. For example, if a depth direction in which an illumination light beam is incident on a specimen is a Z direction, the light beam is scanned in a direction orthogonal to the Z direction, e.g. in an X direction and the imaging is performed, thereby a tomographic image in one cross-section parallel to an XZ plane is obtained. By repeating this while shifting an incident position of the illumination light beam in a Y direction orthogonal to the X direction and Z direction, images of a plurality of cross-sections at positions different in the Y direction can be obtained. For example, if a shift amount in the Y direction is set to be equal to a pixel size of a two-dimensional image corresponding to one cross-section, the data of the pixel has a meaning as voxel data in the three-dimensional image. In this way, the three-dimensional image data of the specimen is obtained.

For example, to obtain a thickness distribution of a cell sheet, it is necessary to perform multi-point observation at a plurality of positions in this cell sheet. For this, it is necessary to obtain a three-dimensional image of the entire cell sheet. However, a plane size of a general cell sheet is considerably larger than an imaging range compatible with an OCT imaging apparatus. Thus, to image the entire cell sheet, the series of imaging operations described above need to be repeated many times while the imaging position is changed, and imaging requires a long time.

Particularly, if this technique is utilized in various tests using a cell sheet as a material or for quality control in a cell sheet manufacturing process, multi-point observation is necessary for each of a multitude of cell sheets, wherefore an enormous amount of imaging time is necessary.

SUMMARY OF THE INVENTION

This invention was developed in view of the above problem and aims to provide a technique for evaluating a cell sheet thickness using the principle of optical coherence tomography imaging, the technique being capable of accurately evaluating the cell sheet thickness while shortening a time required for imaging.

One aspect of this invention is directed to a thickness evaluation method of a cell sheet, comprising tomographically imaging the cell sheet by optical coherence tomography by causing light to be incident on the cell sheet in a direction intersecting a principal surface of the cell sheet; and obtaining a thickness distribution of the cell sheet based on a result of the tomography imaging. A tomographic image corresponding to one cross section of the cell sheet is obtained by the tomography imaging while scanning the light in a main scanning direction, the tomography imaging is performed in every time while moving an incident position of the light in a sub-scanning direction intersecting the main scanning direction at a predetermined feed pitch, thereby a plurality of the tomographic images corresponding to cross-sections at positions different from each other in the sub-scanning direction are obtained. The feed pitch is larger than a size corresponding to one pixel in the tomographic image. One-dimensional thickness distributions of the cell sheet in the corresponding cross-sections are obtained based on each of the plurality of tomographic images, and a two-dimensional thickness distribution of the cell sheet is obtained by interpolating the one-dimensional thickness distributions.

In the invention thus configured, the plurality of tomographic images are obtained while the light incident position is changed at the feed pitch larger than the size equivalent to one pixel in the tomographic image. In optical coherence tomography (OCT) imaging, the feed pitch in the sub-scanning direction is generally about equal to the size equivalent to one pixel (here, referred to as a "pixel size") in the tomographic image to enable the generation of a three-dimensional image of an imaging object. This is because pixel data in the tomographic images directly becomes voxel data in the three-dimensional image by so doing.

However, if such imaging is performed for multi-point observation of a thickness of a cell sheet having a wide area, it takes a long time to image the entire cell sheet. Accordingly, in the invention, the light incident position is moved in the sub-scanning direction at a feed pitch larger than the pixel size. By so doing, a time required to image the entire cell sheet can be shortened.

On the other hand, by increasing the feed pitch, obtainable thickness information becomes discrete in the sub-scanning direction. Accordingly, the two-dimensional thickness distribution is obtained by obtaining the one-dimensional thickness distributions in the obtained tomographic images and performing interpolation in the sub-scanning direction based on the obtained information. If the feed pitch is properly set, a time required for imaging to obtain the thickness can be drastically shortened while a reduction in thickness distribution accuracy is suppressed.

As described above, according to the invention, since a required time is shortened by performing imaging with the feed pitch set larger than that in normal imaging and the two-dimensional thickness distribution is obtained by interpolating the one-dimensional thickness distributions obtained from the plurality of captured tomographic images, the cell sheet thickness distribution can be accurately obtained.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

BRIEF DESCRIPTION OF THE DRAWINGS

FIG. 6 is a flow chart showing a cell sheet thickness distribution calculation process in the embodiment.

DETAILED DESCRIPTION OF THE PREFERRED EMBODIMENTS

Figure 1:
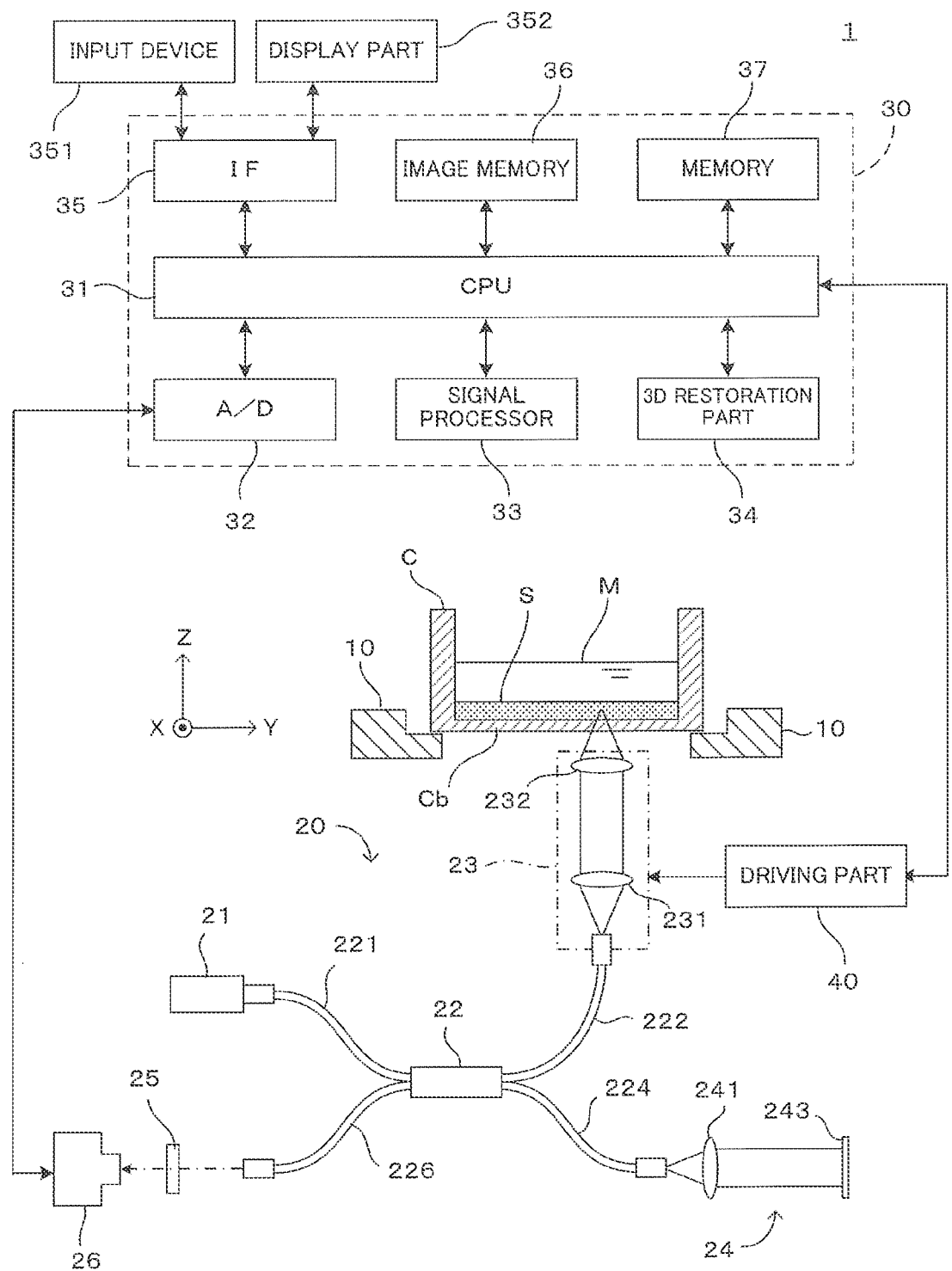
FIG. 1 is a diagram showing a configuration example of an image processing apparatus capable of performing a cell sheet thickness evaluation method according to the invention.

FIG. 1 is a diagram showing a configuration example of an image processing apparatus capable of performing a cell sheet thickness evaluation method according to the invention. This image processing apparatus 1 is an apparatus for imaging cells, a tissue specimen or the like cultured, for example, in a culture solution using an optical coherence tomography (OCT) imaging principle and obtaining a tomographic image. By the image processing of the obtained tomographic image, a cross-section image showing the structure of one cross-section of the specimen can be generated. Further, a three-dimensional image of the specimen can be generated from a plurality of cross-section images. To indicate directions in each figure in a unified manner below, XYZ orthogonal coordinate axes are set as shown in FIG. 1. Here, an XY plane represents a horizontal plane. Further, a Z axis represents a vertical axis, more particularly, a (−Z) direction represents a downward vertical direction.

In this embodiment, a thickness of a cell sheet is automatically evaluated using such an image processing apparatus 1. More specifically, the image processing apparatus 1 tomographically images a cell sheet S carried together with a culture medium M in a specimen container C and obtains a thickness distribution of the cell sheet S using the imaging result. A basic configuration of the apparatus is first described and, thereafter, contents of the thickness evaluation method of this embodiment are described.

The image processing apparatus 1 includes a holder 10. The holder 10 holds the specimen container C for carrying an object to be imaged inside in a substantially horizontal posture with an opening surface of the specimen container C facing upward. Here, a shallow transparent container called an insert well is, for example, used as the specimen container C. An appropriate amount of the culture medium M is poured into the specimen container C. The cell sheet S adhered to and cultured on a bottom surface Cb of the specimen container C is an object to be imaged in this case. Note that a holding mode of the cell sheet S serving as the object to be imaged is arbitrary without being limited to this, but the cell sheet S is desirably so held that a principal surface thereof is substantially horizontal.

The imaging unit 20 is arranged below the specimen container C held by the holder 10. An OCT (Optical Coherence tomography) device capable of capturing a tomographic image of an imaging object in a non-contact and non-destructive (non-invasive) manner is used as the imaging unit 20. As described in detail later, the imaging unit 20, which is an OCT device, includes a light source 21 for generating illumination light to the imaging object, an optical fiber coupler 22, an objective optical system 23, a reference optical system 24, a spectrometer 25 and a photodetector 26.

The image processing apparatus 1 further comprises a control unit 30 which controls an operation of the apparatus and a driving part 40 which drives movable parts of the imaging unit 20. The control unit 3 includes a CPU (Central Processing Unit) 31, an A/D convertor 32, a signal processor 33, a 3D restoration part 34, an interface (I/F) section 35, an image memory 36 and a memory 37.

The CPU 31 governs operations of the entire apparatus by executing a predetermined control program. The control program executed by the CPU 31 and data which are generated during processing are stored in the memory 37. The A/D convertor 32 converts a signal which the photodetector 26 of the imaging unit 20 output in accordance with the amount of received light into digital image data. The signal processor 33 performs image processing described later based upon a digital data outputted from the A/D converter 32, thereby generates the tomographic image of the imaging object. The 3D restoration part has a function for generating a 3D image of the imaging object based on the image data of a plurality of the tomographic images. The image memory 36 saves the image data thus generated. The interface section 35 realizes communication between the image processing apparatus 1 and outside. More specifically, the interface section 35 has a function of communicating with external equipment, and a user interface function of accepting manipulation by a user and informing the user of various types of information. For achieving these objects, the interface section 35 comprises an input device 351 and a display part 352. The input device 351 includes, for instance a key board, a mouse, a touch panel or the like which can accept manipulation and entry concerning selection of the functions of the apparatus, setting of operating conditions, etc. Further, the display part 352 includes a liquid crystal display for example which shows various types of processing results such as the tomographic images generated by the signal processor and the 3D images generated by the 3D restoration part 34.

In the imaging unit 20, from the light source 21 which includes a light emitting element such as a light emitting diode or a super luminescent diode (SLD) for instance, a low-coherence light beam containing wide-range wavelength components is emitted. For imaging the specimen such as cells or the like, an infrared light can be used favorably to make illumination light penetrate into the specimen.

The light source 21 is connected one optical fiber 221 of optical fibers constituting the optical fiber coupler 22. Low-coherence light emitted from the light source 21 is branched into lights to two optical fibers 222, 224 by the optical fiber coupler 22. The optical fiber 222 constitutes an object side optical path. More specifically, light emitted from an end part of the optical fiber 222 is incident on an objective optical system 23.

The objective optical system 23 includes a collimator lens 231 and an objective lens 232. Light emitted from an end part of the optical fiber 222 is incident on the objective lens 232 via the collimator lens 231. The objective lens 232 has a function of converging light (observation light) from the light source 21 to the specimen and a function of condensing reflected light from the specimen and causing the condensed reflected light toward the optical fiber coupler 22. Although a single objective lens 232 is shown in FIG. 1, a plurality of optical elements may be combined. Reflected light from the imaging object is incident as signal light on the optical fiber 222 via the objective lens 232 and the collimator lens 231. An optical axis of the objective lens 232 is orthogonal to the bottom surface of the specimen container C and, in this example, an optical axis direction coincides with a vertical axis direction.

The driving part 40 is controlled by the CPU 31. That is, the CPU 31 gives a control command. In response to this, the driving part 40 makes the imaging unit 20 move in a predetermined direction. More specifically, the driving part 40 makes the imaging unit 20 move in a horizontal direction (XY direction) and a vertical direction (Z direction). The movement in the horizontal direction of the imaging unit 20 causes an imaging range to change in the horizontal direction. The movement in the vertical direction of the imaging unit 20 causes a focus position along the optical axis of the objective lens 232 to change relative to the cell sheet S as the imaging object.

Part of light incident on the optical fiber coupler 22 from the light source 21 is incident on the reference optical system 24 via an optical fiber 224. The reference optical system 24 includes a collimator lens 241 and a reference mirror 243. These constitute a reference system optical path together with the optical fiber 224. Specifically, light emitted from an end part of the optical fiber 224 is incident on the reference mirror 243 via the collimator lens 241. The light reflected by the reference mirror 243 is incident as reference light on the optical fiber 224.

The reflected light (signal light) reflected by a surface or an internal reflecting surface of the specimen and reference light reflected by the reference mirror 243 are mixed in the optical fiber coupler 22 and incident on the photo-detector 26 via the optical fiber 226. At this time, interference due to a phase difference between the reflected light and the reference light occurs, but an optical spectrum of interference light differs depending on a depth of the reflecting surface. That is, the optical spectrum of the interference light has information on a depth direction of the imaging object. Thus, a reflected light intensity distribution in the depth direction of the imaging object can be obtained by spectrally diffracting the interference light at each wavelength to detect a light quantity and Fourier transforming a detected interference signal. An OCT imaging technique based on such a principle is called Fourier domain OCT (FD-OCT).

The imaging unit 20 of this embodiment is provided with a spectroscope 25 on an optical path of the interference light from the optical fiber 226 to the photo-detector 26. A spectroscope utilizing a prism, a spectroscope utilizing a diffraction grating and the like can be, for example, used as the spectroscope 25. The interference light is spectrally diffracted for each wavelength component and received by the photo-detector 26.

By Fourier-transforming the interference signal output from the photo-detector 26 according to the interference light detected by the photo-detector 26, the reflected light intensity distribution of the specimen in the depth direction, i.e. in the Z direction at the incident position of the illumination light is obtained. By scanning the illumination light incident on the specimen container C in the X direction, the reflected light intensity distribution in a plane parallel to an XZ plane is obtained, with the result that a tomographic image of the specimen having this plane as a cross-section can be generated. A principle of generation of the tomographic image is not described because it is known.

Images are obtained by changing the incident position of the light along the Y direction over multiple steps and imaging a tomographic image for every change. By doing so, a number of tomographic images of the specimen are obtained along cross-sectional surfaces which are parallel to the XZ plane. As the scan pitch in the Y direction is reduced, it is possible to obtain image data with sufficient resolution to grasp the stereoscopic structure of the specimen. As just described, the image processing apparatus 1 has a function of generating a cross-section image at an arbitrary cross-section of the cell sheet S serving as the imaging object and a function of generating a three-dimensional image of the cell sheet S from a plurality of images of mutually different cross-sections. Note that, in this specification, if a tomographic image obtained by imaging includes one cross-section of the cell sheet S, that tomographic image may be called a "cross-section image".

Figure 2A:
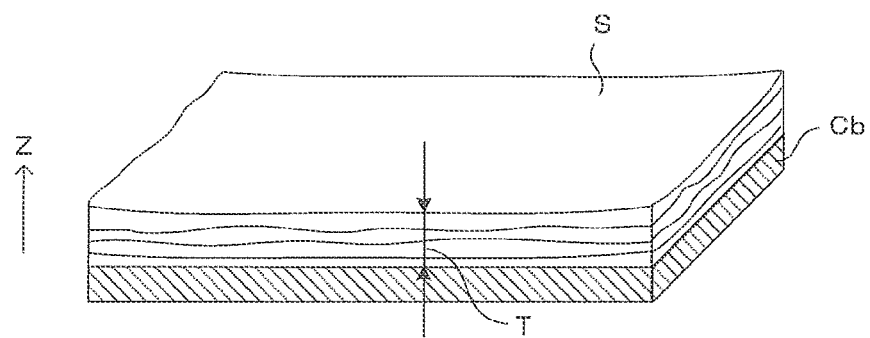
FIGS. 2A and 2B are diagrams schematically showing a structure example of the cell sheet.
Figure 2B:
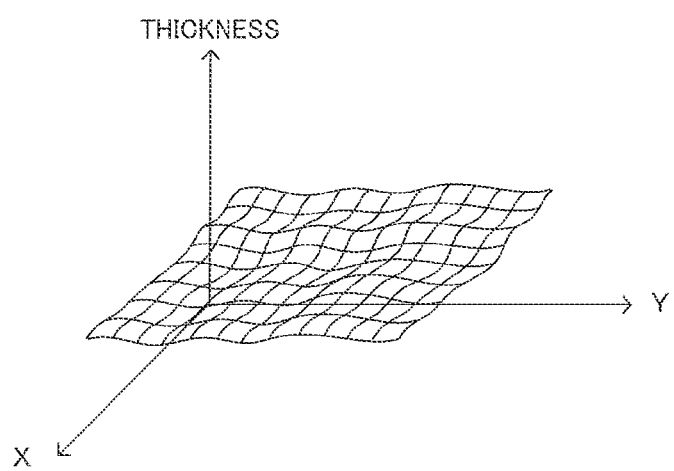

FIGS. 2A and 2B are diagrams schematically showing a structure example of the cell sheet. The cell sheet S is an artificially cultured sheet-like epidermal tissue and widely used as a skin model, for example, for regenerative medicine and drug discovery research. A cell sheet adhered to the bottom surface Cb of the specimen container C is commercially available as the cell sheet S. FIG. 2A schematically shows a cross-sectional structure of the cell sheet S. As shown in FIG. 2A, the cell sheet S is adhered to the bottom surface Cb of the specimen container C and often has a multi-layer structure. Thicknesses of the respective layers vary and a thickness T of the entire cell sheet S also varies.

Such a thickness variation serves as an index indicating the phenotype of the cell sheet S and whether or not a culture state of the cell sheet S is good. Thus, there is a need for accurately obtaining a thickness distribution of the cell sheet S in a non-invasive manner. This embodiment is directed to respond to this need using the OCT imaging technique. That is, this embodiment is designed to obtain the thickness T at each position in the cell sheet S and further obtain two-dimensional thickness distributions in the X and Y directions, i.e. directions along the principal surface of the cell sheet S as shown in FIG. 2B. The thickness T can be obtained, for example, as a size of the cell sheet S in the Z direction if imaging is performed by causing an illumination light beam to be incident in the Z direction with the principal surface of the cell sheet S substantially matched with the XY plane, i.e. the Z direction set as a thickness direction of the cell sheet S. A method for obtaining the two-dimensional thickness distribution of the cell sheet S using the OCT imaging technique is specifically described below.

Figure 3A:
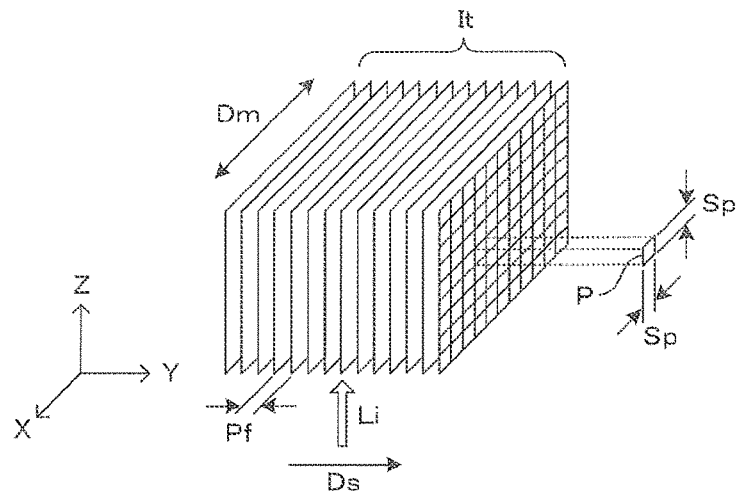
FIGS. 3A to 3C are diagrams showing a concept of three-dimensional image data obtained from results of OCT imaging.
Figure 3B:
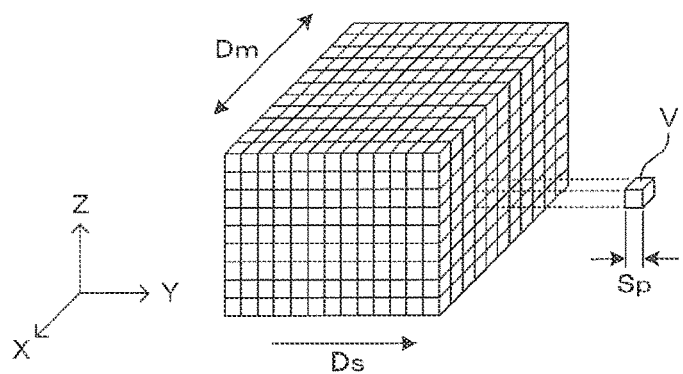
Figure 3C:
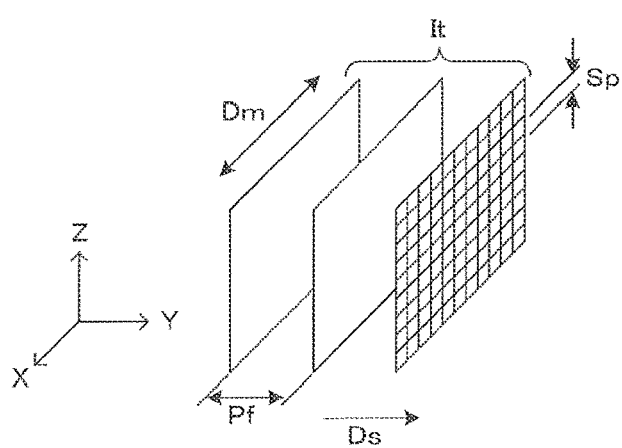

FIGS. 3A to 3C are diagrams showing a concept of three-dimensional image data obtained from results of OCT imaging. In the image processing apparatus 1, an image representing one cross-section parallel to the XZ plane can be obtained by performing imaging while scanning light (observation light) Li incident on the imaging object in the Z direction in the X direction. As shown in FIG. 3A, a scanning direction at this time, i.e. the X direction is referred to as a "main scanning direction" and denoted by Dm. One tomographic image It is composed of a plurality of pixels P two-dimensionally arrayed in the X and Z direction. A size in an actual space corresponding to one pixel (hereinafter, referred to as a "pixel size" and denoted by Sp) can have a minimum value of, e.g. 1 μm although this depends on a magnification of the imaging optical system 23 and a resolution of the optical detector 26. In this case, an effective resolution is about 3 μm.

Tomography imaging is performed every time the incident position of the light Li is changed by a predetermined feed pitch Pf in a sub-scanning direction Ds (Y direction in this example) orthogonal to the main scanning direction Dm. In this way, a plurality of tomographic images It at positions mutually different in the Y direction are obtained. Here, if the feed pitch Pf is set equal to the pixel size Sp, the pixel P of each tomographic image It, which is a two-dimensional image, can be regarded as a pixel (voxel) V in a three-dimensional space having an equal pixel size as shown in FIG. 3B. By doing so, a three-dimensional image can be constructed from a plurality of the tomographic images It. In this way, the three-dimensional structure of the object to be imaged can be grasped.

The two-dimensional thickness distribution of the cell sheet S can be obtained by analyzing the three-dimensional structure from the tomography imaging result of the entire cell sheet S. However, the plane size of the cell sheet S is typically about several mm and sufficiently larger than the size of a cross-section image which can be captured by OCT imaging. Thus, it takes a long time to image the entire cell sheet S if imaging is performed at the feed pitch Pf equal to the pixel size of each tomographic image as described above.

Accordingly, in this embodiment, a time required for imaging is shortened by setting the feed pitch Pf in the Y direction larger than the pixel size Sp with the pixel size Sp in each tomographic image It maintained as shown in FIG. 3C. For example, the feed pitch Pf can be set as an integer multiple of the pixel size Sp. Since a resolution in the Y direction is reduced in this way, measures to suppress measurement errors of the two-dimensional thickness distribution are necessary. For example, the following measure can be taken.

Figure 4A:
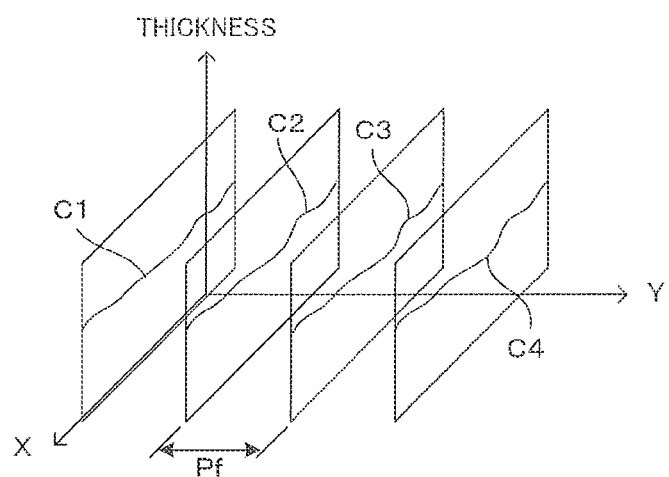
FIGS. 4A and 4B are diagrams showing the principle of two-dimensional thickness distribution measurement in this embodiment.
Figure 4B:
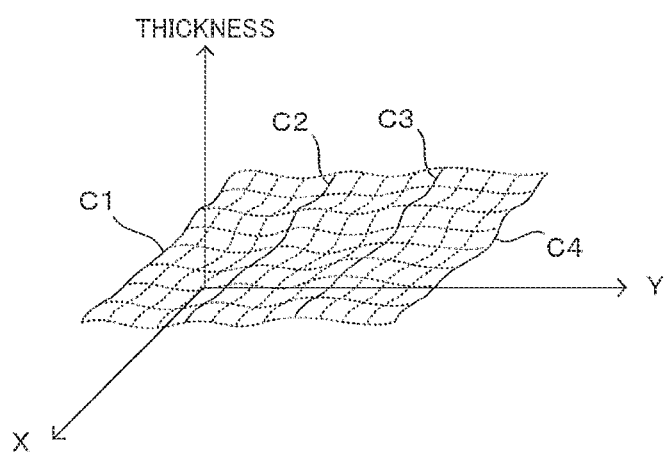

FIGS. 4A and 4B are diagrams showing the principle of two-dimensional thickness distribution measurement in this embodiment. Tomography imaging is performed at the large feed pitch Pf in the Y direction as shown in FIG. 3C and the thickness distribution is obtained in each tomographic image It. Then, as shown in FIG. 4A, thickness distribution curves C1 to C4 representing a thickness change in the X direction are obtained at each position in the Y direction. Thickness information at each position is obtained with a high resolution in the X direction, whereas the thickness information is discrete in the Y direction.

Accordingly, the thickness information obtained from each tomographic image It is interpolated in the X and Y directions. Out of the curves representing the thickness distribution in FIG. 4B, solid lines represent thickness distributions directly obtained from the obtained tomographic images. Further, dotted lines represent thickness distributions obtained by interpolation from that result. The calculation accuracy of the thickness distributions depends on how accurately this interpolation can be performed. Since there is a trade-off relationship between the feed pitch Pf and interpolation accuracy, the feed pitch Pf needs to be properly set. An example of that setting method is described in detail later.

In the description of the above principle, an attempt is made to interpolate in the X and Y directions from one-dimensional thickness distributions accurately obtained in the XZ plane, but coarsely in the Y direction. In this case, interpolation is substantially performed only in the Y direction and interpolation accuracy in the X direction is lower than that in the Y direction. To compensate for this, it would be helpful to have thickness information in an YZ plane by switching the main scanning direction and the sub-scanning direction.

Figure 5A:
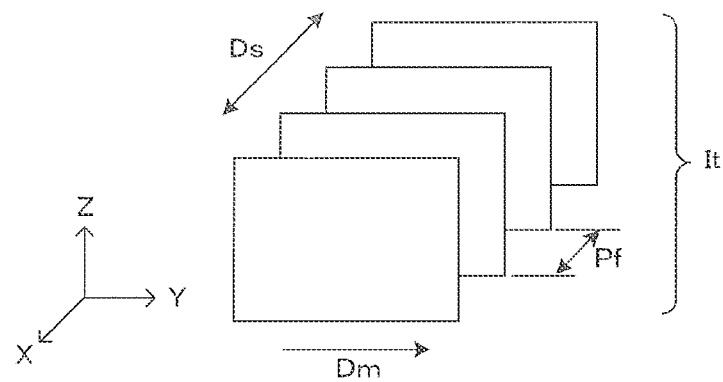
FIGS. 5A and 5B are diagrams showing an example in which the main scanning direction and the sub-scanning direction are switched.
Figure 5B:
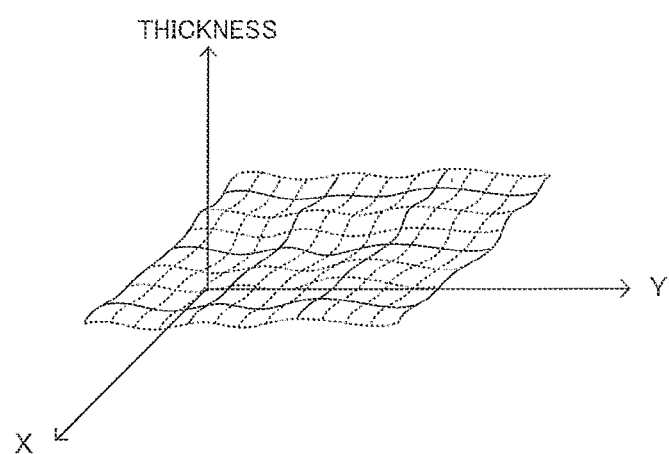

FIGS. 5A and 5B are diagrams showing an example in which the main scanning direction and the sub-scanning direction are switched. Here, tomographic images It for cross-sections parallel to the YZ plane are obtained with the main scanning direction Dm set as the Y direction. In this way, the thickness information in the Y direction can have a high resolution. A light incident position is changed at a relatively coarse feed pitch Pf in the X direction, which is the sub-scanning direction Ds. Therefore, information representing a thickness change in the Y direction is lacking in a region where no tomographic image It is present.

If an imaging result with the X direction set as the main scanning direction Dm and an imaging result with the Y direction set as the main scanning direction Dm are combined, the two-dimensional thickness distribution can be more accurately obtained. That is, as shown in FIG. 5B, the thickness is accurately obtained at each position on solid lines of a mesh. By interpolating the inside of the mesh as indicated by dotted lines in FIG. 5B using those pieces of information, the two-dimensional thickness distribution can be more accurately obtained than interpolation performed merely from one-dimensional thickness distributions.

As just described, the thickness can be, in principle, interpolated in both directions by imaging with either one of the X and Y directions set as the main scanning direction Dm and the other set as the sub-scanning direction Ds. However, for more accurate interpolation, it is desirable to perform imaging with the main scanning direction Dm and the sub-scanning direction Ds switched between the X and Y directions and perform interpolation using those imaging results. Although the feed pitches Pf need not necessarily be equal in the X and Y directions, it is not necessary to make those pitches different unless the imaging object particularly has anisotropy.

The main scanning direction and the sub-scanning direction may be switched, for example, as the scanning direction of the observation light Li and a pitch feed direction are changed. Further, the imaging unit 20 or the imaging object may be rotated 90° about a vertical axis.

FIG. 6 is a flow chart showing a cell sheet thickness distribution calculation process in this embodiment. This process is realized by the CPU 31 executing a control program prepared in advance and causing each component of the apparatus to perform a predetermined operation. Note that, although not particularly distinguished below as long as it is unnecessary, the flow of the process is the same even if only one of the X and Y directions is set as the main scanning direction Dm during imaging or the X and Y directions are set as the main scanning direction Dm in turn. Further, if the cell sheet S has a multi-layer structure, the following process may be performed to individually obtain thickness distributions after the individual layers are distinguished or those layers may be regarded as an integrated structure and an overall thickness distribution may be obtained.

At first, the feed pitch Pf during imaging is set (Steps S101 to S103). First, the input of an instruction on whether the feed pitch Pf is automatically or manually set is received from a user (Step S101). If the user selects automatic setting (YES in Step S101), a pitch determination processing to be described later is performed (Step S102). Unless otherwise (NO in Step S101), a pitch designation is received from the user (Step S103). The pitch designation in this case may be performed, for example, by selecting a default value or by inputting a numerical value. The default value can be, for example, set to be about 10 μm as a numerical value corresponding to the size of cells.

Tomography imaging is performed at the feed pitch Pf thus automatically or manually set (Step S104). As described above, the main scanning direction Dm in imaging may be one of the X or Y direction or may be both directions.

A region corresponding to the cell sheet S is extracted from each of cross-section images representing individual cross-sections obtained by imaging (Step S105). The region can be extracted, for example, as follows. That is, an appropriate threshold value is set in advance for a luminance of each pixel in the image. A region in which a luminance value is within a predetermined range can be regarded as the region of the cell sheet S. Further, for example, each of the structures may be identified by an appropriate classification algorithm obtained in advance by machine learning using morphological features of each layer of the cell sheet S, the culture medium M and the specimen container C appearing in the tomographic images. For example, a semantic segmentation method by deep learning is suitable for such a purpose. Since a specific process of this method is known, it is not described.

After the region of the cell sheet S as a thickness measurement object is extracted from each cross-section image, a thickness distribution (one-dimensional thickness distribution) of the cell sheet S in this cross-section is obtained (Step S106). A thickness at each position can be calculated, for example, based on a continuous length in the Z direction of the extracted region of the cell sheet S. A two-dimensional thickness distribution is obtained by interpolating thickness information at positions where data is not available using data representing the one-dimensional thickness distributions obtained in this way (Step S107). Various known techniques can be used as an interpolation method. For example, spline interpolation can be suitably applied.

In a case where imaging is performed with the main scanning direction Dm and the sub-scanning direction Ds switched between the X and Y directions, two methods for obtaining the two-dimensional thickness distribution are considered. A first method is a method for obtaining an average of thickness distributions individually obtained by interpolation in each of the X and Y directions. A second method is a method for integrating one-dimensional thickness distributions obtained in the X and Y directions and obtaining a thickness distribution by two-dimensional interpolation such as two-dimensional spline interpolation.

An aim of obtaining the two-dimensional thickness distribution of the cell sheet S is accomplished by the process up to this point. The following is an example of a method for presenting this to the user. The obtained two-dimensional thickness distribution of the cell sheet S can be represented by a mesh pattern, for example, as shown in FIG. 2B. Besides, the thickness distributions can be presented by a two-dimensional map in which a thickness is replaced by a luminance as described next.

That is, the thickness at each position obtained by interpolation is converted into a luminance value to be given to the pixel at this position (Step S108). The thicknesses may be converted into the luminance values in proportion to the thicknesses or the thicknesses may be replaced by luminance values in multiple stages. Further, the thicknesses may be represented by colors. The pixel having the luminance value corresponding to the thickness given thereto is arranged at a corresponding position on a two-dimensional image plane. In this way, the two-dimensional map representing the thickness distributions by luminance values can be generated (Step S109). By displaying this map on the display part 352 (Step S110), for example, the two-dimensional thickness distribution can be visualized and presented to the user.

Next, the pitch determination processing performed in Step S102 is described. This processing is a processing for optimizing the feed pitch Pf according to the imaging object with the trade-off constraints with the thickness distribution calculation accuracy. This processing is realized by the CPU 31 executing the control program prepared in advance and causing each component of the apparatus to perform a predetermined operation.

Figure 7:
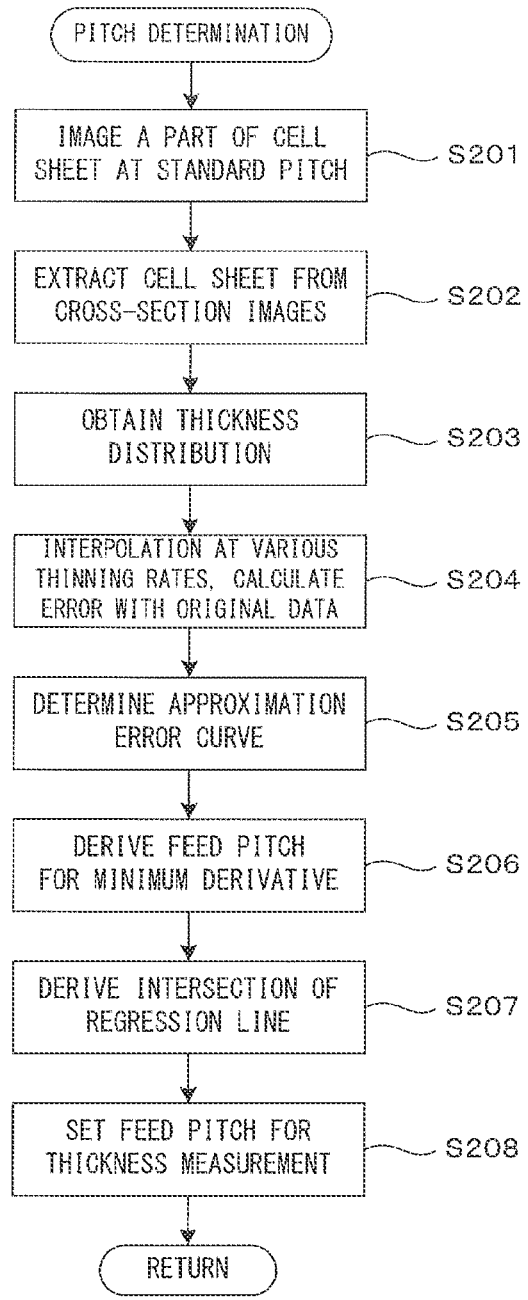
FIG. 7 is a flow chart showing the pitch determination processing.

FIG. 7 is a flow chart showing the pitch determination processing. At first, a partial region of the cell sheet S is tomographically imaged at a standard pitch (Step S201). Each tomographic image at this time is referred to as a "partial tomographic image" in this specification. The "standard pitch" is a feed pitch in normal tomography imaging to obtain a three-dimensional image of an imaging object, and the size thereof is equivalent to the pixel size (e.g. 1 μm). Although it takes a long time to image the entire cell sheet S at the standard pitch, the imaging time can be relatively short since an imaging range is narrow in this imaging. For example, a region of about 100 μm in each of the X and Y directions can be set as the imaging range.

In the image processing apparatus 1, it is desirable to set a feed pitch corresponding to a voxel size at least smaller than the size of cells as the standard pitch if a resolution (or voxel size) in imaging can be changed and set. For example, an imaging mode having a highest resolution (i.e. the voxel size is minimum) can be used.

Also in this case, imaging may be performed with only either one of the X and Y directions set as the main scanning direction Dm, or the main scanning direction and the sub-scanning direction may be switched and imaging may be performed in each case.

Similarly to the two-dimensional thickness distribution calculation process described above, a region occupied by the cell sheet S is extracted from each captured tomographic image (partial tomographic image) (Step S202). Further, a one-dimensional thickness distribution in the cross-section image is obtained for the extracted region of the cell sheet S (Step S203).

The data of the one-dimensional thickness distribution of each cross-section thus obtained at the standard pitch is thinned at a certain rate in the pitch feed direction. Moreover, thickness data lost by thinning is obtained by interpolation and an error is calculated by the comparison of the obtained data with the original data before thinning. This processing is performed at various thinning rates (Step S204).

Figure 8:
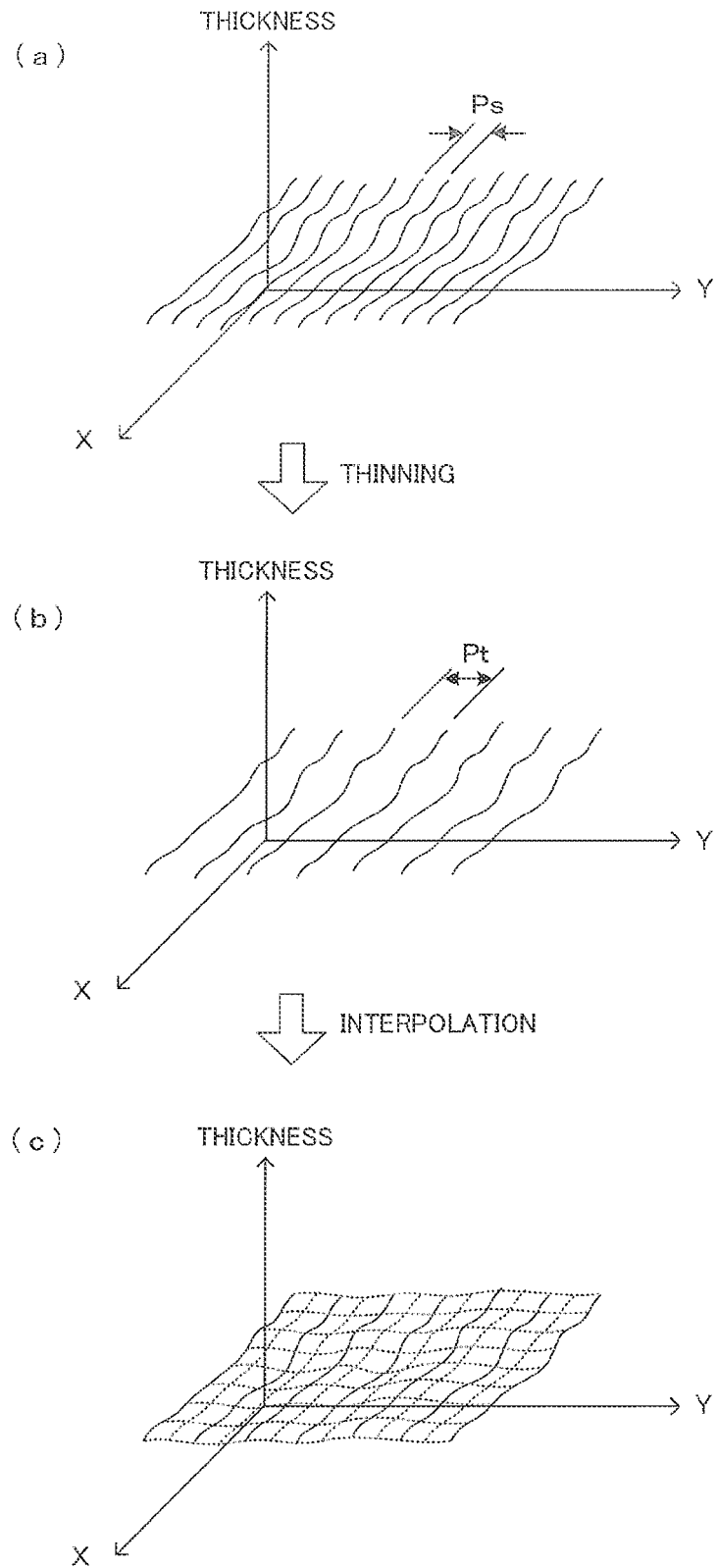
FIG. 8 shows diagrams illustrating thinning and interpolation processes.

FIG. 8 shows diagrams illustrating thinning and interpolation processes. The one-dimensional thickness distributions obtained at the standard pitch Ps as shown by (a) in FIG. 8 are thinned at a certain rate. In this way, as shown by (b) in FIG. 8, the one-dimensional thickness distributions more discrete from each other are obtained. Since the pitch feed direction is the Y direction in this example, intervals in the Y direction become larger by thinning. By performing the interpolation processing for this, the restoration of the thinned data is attempted as shown by (c) of FIG. 8. If an error at this time is small, it can be said that thinning does not largely affect the two-dimensional thickness distribution calculation accuracy. That is, it can be said that the two-dimensional thickness distribution can be obtained with sufficient accuracy by setting the interval Pt after thinning as the feed pitch Pf during imaging.

Figure 9A:
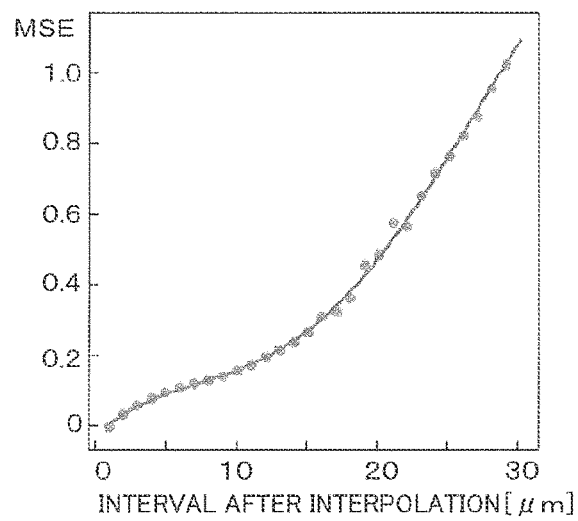
FIGS. 9A to 9C are graphs showing relationships of the thinning rate and the error.
Figure 9B:
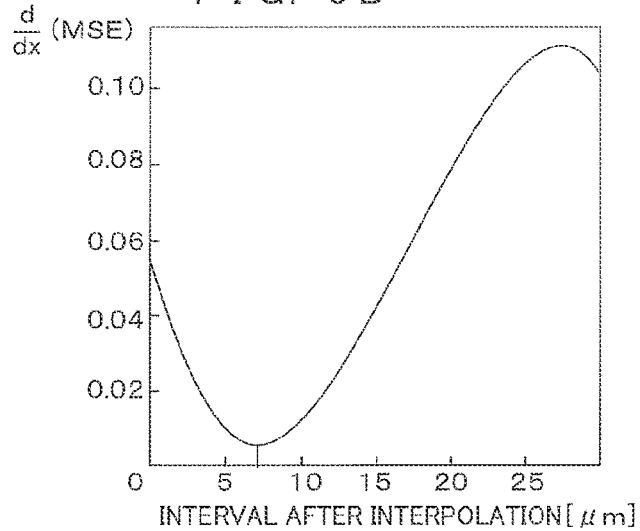
Figure 9C:
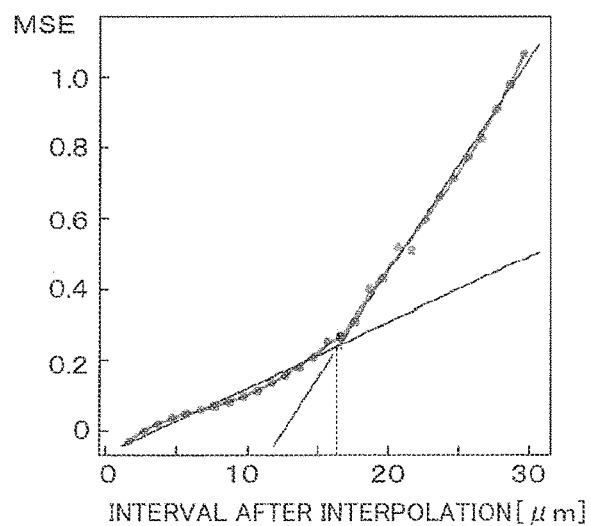

FIGS. 9A to 9C are graphs showing relationships of the thinning rate and the error. In FIGS. 9A to 9C, a horizontal axis represents the interval Pt after thinning when the thinning rate was changed to (½), (⅓), . . . with the standard pitch set to 1 µm. If images captured at a feed pitch of 1 µm are thinned, for example, at the thinning rates (½), (⅓), the intervals Pt between the images after thinning are respectively 2 µm, 3 µm. That is, thinning at the thinning rate (1/N) means the extraction of one image out of N images. Therefore, as a degree of thinning increases, a numeral value of the thinning rate becomes smaller. Note that it is focused in this embodiment to evaluate with the degree of thinning variously changed, and the definition of the thinning rate is not important.

A vertical axis of FIG. 9A represents a mean square error (MSE) between the thickness after interpolation and the thickness in the original data before thinning. As the degree of thinning increases, the error monotonously increases since more data is missing. However, a degree of increase is not linear and it is found that there is a region in an intermediate part where an error increase rate is moderate before and after the intermediate part.

A change of this error is approximated by an appropriate polynomial (Step S205) and this polynomial is differentiated. Then, as shown in FIG. 9B, a derivative value has a local minimum in a region where the error moderately increases. In the first method for obtaining the optimal value of the feed pitch Pf, the thinning rate when the derivative value becomes minimum is set as the feed pitch Pf in imaging at the time of thickness distribution calculation (Step S206). Then, it is thought that loss of the thickness information can be suppressed to a minimum level while the imaging time is shortened by the expansion of the feed pitch. Since the local minimum is reached when the interval after thinning is about 7.1 µm in this example, the feed pitch Pf may be set to this value (or a rounded value of 7 µm).

On the other hand, as the second method for obtaining the optimal value of the feed pitch Pf, it is considered to approximate a calculation result of MSE by two regression lines and obtain an intersection of these lines as shown in FIG. 9C (Step S207). This assumes such a characteristic that original information is maintained relatively well and, hence, an error is relatively small if the degree of thinning is small, but the error suddenly increases if the degree of thinning increases and information relating to the individual cells is lost. In this example, the intersection of the regression lines is at a position of about 17 µm as the interval after thinning.

Here, the larger the feed pitch Pf during imaging, the shorter the imaging time and the larger the interpolation error. Conversely, the smaller the feed pitch Pf during imaging, the longer the imaging time, but the smaller the interpolation error. Accordingly, it can be said that the larger one of the optimal values of the feed pitch Pf obtained by the above two methods is an optimal value when a processing speed (required time) is prioritized, and the smaller value is an optimal value when the interpolation accuracy is prioritized.

In an actual processing, which of them is prioritized depends on the purpose of the processing. Accordingly, for example, the optimal values can be respectively calculated by the two methods, the calculated optimal values can be presented as candidates for the optimal set value to the user, and the user can be caused to select the set value in a range between the both values. The value of the feed pitch Pf determined in this way is set as a value applied for imaging when the two-dimensional thickness distribution of the entire cell sheet S is obtained (Step S208).

In the case where imaging is performed with the main scanning direction and the sub-scanning direction switched, the aforementioned relationship of the thinning rate and the error can be derived by applying the same thinning rate in the X and Y directions. Then, optimal values can be similarly obtained. By performing imaging with the pitch feed in two different directions, it may be possible to suppress a reduction in the thickness distribution calculation accuracy even with coarser thinning than in the case of the pitch feed in one direction.

Note that the size of the cells constituting the cell sheet S is typically about 10 µm. Accordingly, with the feed pitch Pf larger than this, information on a thickness change caused by the individual cells is lost and the interpolation accuracy is thought to be drastically reduced. Because of this, an upper limit value of the feed pitch Pf may be determined in advance and the feed pitch Pf may be set without exceeding the upper limit value regardless of the calculated optimal value.

Further, in a case where a thickness distribution is obtained for each layer of the cell sheet S having a multi-layer structure, candidates for the optimal value are calculated by the above two methods for each layer. Then, a minimum value of a plurality of candidate values calculated for each layer by the first calculation method is set as a candidate for the optimal value by the first method. Further, a minimum value of a plurality of candidate values calculated by the second calculation method is set as a candidate for the optimal value by the second method. Then, these candidates for the optimal value may be presented and the user may be caused to determine a final set value.

Note that the invention is not limited to the above embodiment and various changes other than the aforementioned ones can be made without departing from the gist of the invention. For example, in the above embodiment, the thickness distribution of the cell sheet S adhered to the bottom surface of the specimen container C such as an insert well is evaluated. However, a support mode of the cell sheet S is arbitrary without being limited to this. Further, this method can be utilized for the purpose of evaluating a thickness of a specimen such as a cell colony adhered and cultured on a container wall surface, besides the cell sheet S.

Further, for example, the calculated two-dimensional thickness distribution of the cell sheet is presented as the two-dimensional map to the user in the above embodiment. However, the usage of the obtained two-dimensional thickness distribution is not limited to this. For example, the thickness distribution can be processed by an appropriate statistical method and used for the purpose of evaluating a variation.

Further, for example, whether the feed pitch Pf at the time of measuring the thickness distribution is set by the user or automatically set by the pitch determination processing is selectable in the above embodiment. However, for example, the result of the pitch determination processing performed in the past for the same type of specimens may be used. Further, in evaluating a plurality of the same type of specimens, it is not always necessary to set the pitch for each individual specimen. For example, the feed pitch set for the first specimen can be also applied to the other specimens.

Further, for example, the imaging of the partial tomographic image in the pitch determination processing may be performed at a plurality of positions in the cell sheet S. By so doing, the influence of a local thickness abnormality on the evaluation result of the entire cell sheet S can be suppressed.

Further, for example, the method for determining the feed pitch using the error between the thickness distribution after interpolation and the actually measured thickness distribution in the pitch determination processing is not limited to the above. For example, a method for determining the magnitude of an allowable error in advance and adopting a largest feed pitch within a range not exceeding the allowable error is considered.

Further, for example, the above embodiment relates to a so-called Fourier-domain OCT imaging apparatus for obtaining a reflection light intensity distribution in a depth direction from the intensity of interference at each wavelength using observation light including wavelength components in a wide range. However, besides this, the invention is applicable to various imaging apparatuses for tomography imaging using the OCT imaging principle such as a time domain OCT imaging apparatus.

Further, as the control unit 30 of the above embodiment, it is also possible to use a general-purpose processing device having a general configuration such as a personal computer or work station. That is, the image processing apparatus 1 may be configured by combining an imaging apparatus including the imaging unit 20 and the driving part 40 and having a minimum control function for operating these and a personal computer or the like functioning as the control unit 30 by executing the control program describing the above processing contents.

As the specific embodiment has been illustrated and described above, the thickness evaluation method of the cell sheet according to the invention may further include capturing a plurality of partial tomographic images corresponding to parts of the cell sheet by moving the light incident position in the sub-scanning direction at an interval smaller than the feed pitch, obtaining the one-dimensional thickness distributions of the cell sheet in cross-sections corresponding to the partial tomographic images and setting the feed pitch based on the obtained result. According to such a configuration, since the feed pitch can be determined in consideration of how the thickness actually varies in the cell sheet, the accuracy of the evaluation result can be improved.

More specifically, for example, some of the captured partial tomographic images can be thinned at a certain rate in the sub-scanning direction, the one-dimensional thickness distributions of the cell sheet in the partial tomographic images after thinning can be interpolated in the sub-scanning direction, and the feed pitch can be set based on errors between the thicknesses obtained by interpolation and actually measured thicknesses in the thinned partial tomographic images. The error between the interpolated value and the actually measured value is expected to increase due to data missing caused by thinning. From this, if the feed pitch is set while the magnitude of the error is evaluated, a time required for imaging can be shortened while the error in thickness distribution calculation is suppressed to a predetermined range.

In this case, an approximation curve representing a change of the error can be obtained using the thinning rate as a variable and a thinning interval when a derivative value of the approximation curve becomes minimum can be set as the feed pitch. Alternatively, a change of the error when the thinning rate is used as a variable can be approximated by two regression lines corresponding to a side where the thinning interval is large and a side where the thinning interval is small and the thinning interval corresponding to an intersection of these lines can be set as the feed pitch. According to the knowledge of the present inventor, the value of the feed pitch capable of combining the shortening of the imaging time and the thickness distribution calculation accuracy can be derived by these methods.

Further, for example, in determining the feed pitch, the main scanning direction and the sub-scanning direction may be switched and the partial tomographic images may be captured before and after that switch. By so doing, the feed pitch can be more properly determined than evaluation only in one direction.

Similarly, in obtaining the two-dimensional thickness distribution of the cell sheet, tomographic images may be further captured with the main scanning direction and the sub-scanning direction switched, and one-dimensional thickness distributions obtained for the respective tomographic images may be two-dimensional interpolated to obtain the two-dimensional thickness distribution. By so doing, the accuracy of interpolation can be further improved and accuracy in calculating the two-dimensional thickness distribution can also be improved.

This invention is suitably applicable for the purpose of evaluating a thickness distribution of an artificially cultured cell sheet and suitable, for example, in fields of regenerative medicine and drug discovery research.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. A thickness evaluation method of a cell sheet, comprising:
   capturing a plurality of tomographic images of the cell sheet using optical coherence tomography by causing light to be incident on the cell sheet in a in a direction intersecting a principal surface of the cell sheet; and
   obtaining a thickness distribution of the cell sheet based on a result of the tomography imaging, wherein the imaging step includes:
  scanning repeatedly the light in a main scanning direction while moving an incident position of the light in a sub-scanning direction intersecting the main scanning direction at a feed pitch larger than a size corresponding to one pixel in the tomographic images; and
  capturing a tomographic image of the cell sheet at each scan in the main scanning direction, thereby generating the plurality of the tomographic images corresponding to cross-sections at positions different from each other in the sub-scanning direction,
wherein the obtaining step includes:
  obtaining one-dimensional thickness distributions of the cell sheet in the corresponding cross-sections based on each of the plurality of tomographic images; and
  obtaining a two-dimensional thickness distribution of the cell sheet by interpolating the one-dimensional thickness distributions, and
wherein the method further comprises:
  capturing a plurality of partial tomographic images corresponding to a partial region of the cell sheet while moving the light incident position in the sub-scanning direction at a standard interval determined in advance,
  obtaining the one-dimensional thickness distributions of the partial region in cross-sections corresponding to the partial tomographic images, and
  setting the feed pitch larger than the standard pitch based on the obtained one-dimensional thickness distributions.

2. The thickness evaluation method of the cell sheet according to claim 1, further comprising:
  thinning of the partial tomographic images at a certain rate;
  interpolating the one-dimensional thickness distributions of the cell sheet in the sub-scanning direction based on the partial tomographic images remained after thinning; and
  setting the feed pitch so that errors between the thicknesses obtained by interpolation and actually measured thicknesses in the thinned partial tomographic images do not exceed an allowable error in advance.

3. The thickness evaluation method of the cell sheet according to claim 2, wherein
  an approximation curve representing a change of the error is obtained by polynomial approximation using a thinning interval as a variable, the thinning interval being an interval between the partial tomographic images after thinning, and
  a value of the thinning interval when a derivative value of the approximation curve becomes minimum is set as the feed pitch.

4. The thickness evaluation method of the cell sheet according to claim 2, wherein
  a change of the error by two regression lines corresponding to mutually different ranges of a thinning interval is performed using the thinning interval as a variable, the thinning interval being an interval between the partial tomographic images after thinning, and
  a value of the thinning interval corresponding to an intersection of the two regression lines is set as the feed pitch.

5. The thickness evaluation method of the cell sheet according to claim 1, wherein
  the main scanning direction and the sub-scanning direction are switched and the partial tomographic images are imaged before and after that switch, and
  the feed pitch is set based on the one-dimensional thickness in two directions.

6. A thickness evaluation method of the cell sheet comprising:
  capturing a plurality of tomographic images of the cell sheet using optical coherence tomography by causing light to be incident on the cell sheet in a direction intersecting a principal surface of the cell sheet; and
  obtaining a thickness distribution of the cell sheet based on a result of the tomography imaging,
wherein the imaging step includes:
  scanning repeatedly the light in a main scanning direction while moving an incident position of the light in a sub-scanning direction intersecting the main scanning direction at a feed pitch larger than a size corresponding to one pixel in the tomographic images; and
  capturing a tomographic image of the cell sheet at each scan in the main scanning direction, thereby generating the plurality of the tomographic images corresponding to cross-sections at positions different from each other in the sub-scanning direction,
wherein the obtaining step includes:
  obtaining one-dimensional thickness distributions of the cell sheet in the corresponding cross-sections based on each of the plurality of tomographic images; and
  obtaining a two-dimensional thickness distribution of the cell sheet by interpolating the one-dimensional thickness distributions,
wherein tomographic images in which the main scanning direction and the sub-scanning direction are switched are further imaged, and
wherein the two-dimensional thickness distribution is obtained by two-dimensional interpolation using one-dimensional thickness distributions obtained for the respective tomographic images imaged before and after that switch.

* * * * *